United States Patent [19]

Bee et al.

[11] Patent Number: 5,258,184

[45] Date of Patent: * Nov. 2, 1993

[54] EMULSIONS

[75] Inventors: Rodney D. Bee, Cambridgeshire; Ian D. Evans, Bedford; Martin J. Izzard, Northants, all of England

[73] Assignee: Unilever Patent Holdings B.V., Rotterdam, Netherlands

[*] Notice: The portion of the term of this patent subsequent to Jan. 15, 2008 has been disclaimed.

[21] Appl. No.: 929,495

[22] Filed: Aug. 18, 1992

Related U.S. Application Data

[63] Continuation of Ser. No. 610,066, Nov. 7, 1990, abandoned, which is a continuation of Ser. No. 361,051, Jun. 5, 1989, Pat. No. 4,985,250.

[30] Foreign Application Priority Data

Jun. 3, 1988 [GB] United Kingdom ............... 8813161.0

[51] Int. Cl.⁵ ................................................ A61K 9/113
[52] U.S. Cl. ................................ 424/401; 424/439; 424/455; 514/937; 514/943; 426/602
[58] Field of Search ................ 424/401, 439, 455; 514/937, 938, 939, 943, 941; 426/602

[56] References Cited

U.S. PATENT DOCUMENTS

| | | | |
|---|---|---|---|
| 4,254,105 | 3/1981 | Fukuda | 514/943 |
| 4,379,755 | 4/1983 | Yamada et al. | 514/943 |
| 4,714,566 | 12/1987 | Takahashi et al. | 514/943 |
| 4,933,192 | 6/1990 | Darling et al. | 426/98 |

FOREIGN PATENT DOCUMENTS 0239378 4/1987 European Pat. Off.
2165163 4/1986 United Kingdom.

Primary Examiner—Thurman K. Page
Assistant Examiner—James M. Spear
Attorney, Agent, or Firm—Cushman, Darby & Cushman

[57] ABSTRACT

The invention provides a water/oil/water duplex emulsion in which the external continuous phase is gelled. This gelling is obtained by having an osmotic pressure component, e.g. an electrolyte, in the internal aqueous phase which draws water from the external phase through the oil phase. The structure is firm but contains a considerable volume of available aqueous phase. The structure is of value in e.g. foods and cosmetics.

9 Claims, No Drawings

EMULSIONS

This is a continuation of application Ser. No. 07/610,066, filed on Nov. 7, 1990, which was abandoned upon the filing hereof which is a continuation of Ser. No. 07/361,051, filed Jun. 5, 1989 (now U.S. Pat. No. 4,985,250).

FIELD OF THE INVENTION

This invention relates to duplex emulsions of the water/oil/water (WOW) type. Emulsions of this class comprise an aqueous phase dispersed in an oil phase which is, in turn, within an outer continuous aqueous phase. Such systems are also termed multiple emulsions. These systems have utility in e.g. foods, drug deliveries, creams and cosmetics intended for topical application.

BACKGROUND TO THE INVENTION

Water/oil/water emulsions have been available for many years and it has been appreciated they can provide release systems, eg. for perfumes, cosmetic active ingredients and flavours, and control of rheology.

GENERAL DESCRIPTION OF THE INVENTION

The invention provides a gelled duplex emulsion structure comprising
 i) 0.1% to about 40% by weight of a gelled external continuous aqueous phase,
 ii) oil or substantially liquid fat component, preferably edible, dispersed in the external phase and
 iii) an aqueous phase containing an osmotic pressure component and dispersed in the oil or substantially liquid fat phase.

The duplex emulsion structure is thus characterised by having a gelling component in the external aqueous phase and an osmotic pressure component in the internal aqueous phase. In the product the gelled external phase preferably forms at least 1% of the structure and preferably up to about 20% by weight. The oil/fat phase will usually form from about 5% to about 30% by weight of the total composition, preferably from about 10% to about 20%.

In these novel gel structures droplets of a free aqueous solution are retained within a three dimensional gel network. This structure is obtained with low levels of a gelling component because the latter is present as a concentrated gel in the lamellae between the droplets of the swollen w/o emulsion, thus forming a three dimensional network through the structure. Thus a structure containing a high proportion of ungelled aqueous solution is provided. The concentration of gelling component in the lamellae is relatively high although the initial external aqueous phase has a lower concentration. Usually the claimed combination of gelling agent and swelling duplex emulsion provide a gelling time from a few minutes to several hours. Thus a structure is provided which is formed in situ to give a firm structure with a relatively high volume of available dispersed liquid phase.

Preferably the external continuous aqueous phase also contains an osmotic pressure component to control the rate of osmosis until osmotic balance is achieved. The presence of an external osmotic pressure component allows the progress to osmotic balance to be controlled more exactly. The gel structure obtained is effective even if in time the total structure forms a network in which some of the discrete volumes within the gel become connected as the gel membranes between them breakdown.

A fat component is usable, but in this duplex form the emulsion would be formed above the fat melting point, where the phase is substantially liquid, and retained there while osmosis and gelling occurred. The final structure would, in this case, comprise a solid fat phase formed as the gelled structure is cooled to ambient.

In one embodiment of the structure reactive species can be retained separate as different aqueous solutions in internal aqueous phases. These species are brought into contact to produce, eg. a colour change, when the gel structure is ruptured.

Thus the invention includes a method of preparing a gelled duplex emulsion structure wherein a water in oil/fat emulsion, having an osmotic pressure component in the aqueous phase, is dispersed in a solution of a gelling component, preferably containing about 0.1% to about 5%, usually up to about 2% by weight of the component, and the emulsion retained until the external continuous phase has gelled.

Gelling of the external aqueous phase can be achieved by release of a solute from the internal aqueous phase. Speed of release and thus gelling is dependent, inter alia, on the size of internal aqueous and oil droplets, concentration gradient across the oil membrane and emulsifier concentrations. Thus control of gelling is obtained by varying these features. The term "gelling" is used herein to include physical setting by thermal or chemical means.

Osmotic swelling of the water in oil emulsion in the systems of the invention prepared from i) self gelling components and ii) those requiring cation release causes the gelling component to be increased in concentration. However for cation sensitive gelling the major factor in gelling is the controlled release of the cation from the internal water phase, although an increase in concentration of the gelling component also occurs.

Further control of the swelling and release rates can be obtained by having a separate osmotic swelling component in the droplets from which the desired component is to be released to cause gelling of the external phase. That is, the internal aqueous phase can comprise two types of droplets.

COMPONENTS OF THE INVENTION

The internal aqueous phase containing the osmotic pressure component is dispersed in the oil/fat phase which is, in turn, dispersed in the external continuous phase containing the gelling component.

Examples of the oils and fats are olive oil, palm oil, groundnut oil, sunflower oil and animal fats, for example tallow and lard.

An internal emulsifier is required to stabilize the water in oil emulsion and will normally have a hydrophilic-lipophilic balance (HLB) of not more than 6, preferably not more than 5. Examples of these emulsifiers are the polyglycerol esters of fatty acids, optionally polymerised fatty acids. Another suitable emulsifier is polyglycerol polyricinoleic acid obtainable from Quest International Limited of Ashford, England under the trade name Admul WOL. Other examples of emulsifiers are sorbitan mono-oleate and analagous esters, sucrose esters and lecithin dependent on the other components. Alternatively the internal phase may be stablilized by solid particles with appropriate surface properties which move to the W/O interface. The internal emulsifier is capable of stabilizing the water/oil emulsion in the first emulsion stage when the oil containing the dispersed aqueous phase is emulsified in the external aqueous phase.

The external oil/water emulsifier will normally have an HLB of at least 8 and examples are polyoxyethylene sorbitan esters. Other emulsifiers are proteins, for example milk proteins, blood proteins and egg proteins. The emulsifier stabilizes the oil droplets as a dispersion in the continuous aqueous phase. Other materials usable as the external o/w emulsifier are diacetyl tartaric acid esters of monoglycerides (E472E), sucrose esters and stearoyl lactylates.

The internal aqueous phase is required to include an osmotic pressure component which generates an osmotic gradient between the internal and external aqueous phases. This osmotic pressure component will be water soluble with a relatively low oil solubility. Examples of this component are salts, e.g. sodium chloride, sugars, for example glucose, sucrose and malto-dextrins; other solutes are amino acids and peptides. Urea, a component of value in skin humectant compositions, may also be used.

The gelling component in the external continuous phase is required to form a gel because its concentration increases with movement of water through the oil/fat semi-permeable membrane or be gelled during or after being concentrated by this process by any conventional gelling process which may be brought about by, for example, cooling, heating or chemical reaction. Gelling may be accelerated or achieved by interaction with an appropriate cation released from the internal aqueous phase. Examples of the gelling component are gelatin and meat, egg and fish proteins, gelling polysaccharides, for example, xanthan/galactomannan mixtures, k-carrageenan/potassium and alginate/calcium. Additionally particulate inorganic materials, e.g. laponite clays, are usable as the gelling component.

SPECIFIC DESCRIPTION OF THE INVENTION

Examples of the duplex emulsions of the invention will now be given to illustrate but not limit the invention.

EXAMPLE I

Examples of four duplex emulsions of the invention were prepared and their compression characteristics compared with an oil in water emulsion of the same overall composition.

In these formulations the external continuous aqueous phase had the initial composition (w/w):

| | |
|---|---|
| sodium caseinate | 1% |
| gelatin (250 Bloom) | 1% |
| sucrose | 1% |
| water | 97% |

The caseinate functions as the oil in water emulsifier.

Two water in oil emulsions A and B were prepared by emulsifying 30 g of a sucrose solution into groundnut oil (50 g) with the aid of Admul WOL (5 g) as emulsifier. The latter is polyglycerol polyricinoleic acid obtainable from Quest International of Ashford England. Emulsification was achieved using a Silverson mixer (type L2R) on full power with a fine emulsor screen for 5 minutes. The two emulsions differed by the concentration of sucrose in the aqueous solution. Solution A contained 30% w/w sucrose and solution B was 70% w/w sucrose.

Four duplex emulsions were prepared by emulsifying two amounts of emulsions A and B into the external phase solution by gently shearing with a Silverson mixer at low (¼) power for 10 to 40 secs. For purposes of comparison equivalent amounts of groundnut oil were emulsified into the external phase solution to provide oil in water single emulsions. The sucrose component acted to draw water from the continuous phase into the internal aqueous phase through the oil layer under osmotic drive.

The initial phase volumes of the w/o emulsion is approximately in the range 0.2–0.3. After osmotically driven swelling of the internal aqueous phase these formulations theoretically produce disperse phase volumes approximately in the range 0.7–0.9. However, in practice, a small proportion of the internal phase is lost in preparation and during osmotic swelling so the actual volume of dispersed phase is somewhat lower than calculated theoretically.

These six emulsions were prepared at 45° C., poured into moulds and allowed to set overnight (8–16 hrs) at 5° C. The four duplex emulsions set more rapidly than the two single emulsion comparisons and a sample of the external phase.

The compression characteristics of the gelled materials was tested using an Instron compression tester at 5° C. The results, given in Table I, demonstrate the duplex emulsions of the invention provide stronger gels. The force (Newtons) registered when a sample was compressed to 50% of original height was noted.

TABLE I

| Example | Physical Form | External Phase | Internal Phase | Force (Newtons) |
|---|---|---|---|---|
| 1 | duplex | 200 g | Emulsion A 50 g | 0.433 |
| 2 | duplex | 200 g | Emulsion B 50 g | 0.400 |
| 3 | duplex | 200 g | Emulsion A 75 g | 0.367 |
| 4 | duplex | 200 g | Emulsion B 75 g | 0.463 |
| 5* | oil in water | 200 g | Groundnut Oil 29 g | 0.116 |
| 6* | oil in water | 200 g | Groundnut Oil 44 g | 0.125 |
| 7* | solution | (external phase) | | 0.056 |

*Comparison

So as to further indicate the novel properties of cellular gels the viscoelastic behaviour has been compared with simple gels of the same overall composition (excluding the w/o emulsifier and the sucrose component of the internal water phase). The formulations are shown below:

| | |
|---|---|
| External phase(s): | |
| Sodium caseinate | 1 g |
| Sucrose | 1 g |
| Gelatin | 0.3, 0.6, 1 g |
| Water | to 100 g |
| Internal phase(s): | |
| Groundnut oil | 50 g |
| Admul WOL | 5 g |
| Sucrose solution (30% w/w) | 30 g |

Measurements were made at 0.1 hertz after setting at 5° C. for 1 hour. The results are given in Table II.

It is clear that the elastic modulus of these gelled emulsions is very much higher at a given gelatin concentration than the gel formed from the o/w emulsion of similar composition. Secondly, the phase angle (d) is much larger for these gels than for the equivalent gelled oil in water emulsions. The ratio of the loss to storage modulus (tan d) is much larger for these gels, indicating them to have additional energy dissipation modes. These presumably include the viscous flow of liquid inside the swollen duplex droplets.

TABLE 2

| EXAMPLE | PHYSICAL FROM | EXTERNAL PHASE | DISPERSED PHASE | ELASTIC MODULUS $(Nm^{-2})$ | LOSS MODULUS $(Nm^{-2})$ | d | TAN d |
|---|---|---|---|---|---|---|---|
| 8 | Duplex | 200 g - 0.3% gelatin | 75 g w/o | 33.6 | 13.6 | 22 | 0.404 |
| 9 | Duplex | 200 g - 0.6% gelatin | 75 g w/o | 401 | 85.2 | 12 | 0.213 |
| 10 | Duplex | 200 g - 1% gelatin | 75 g w/o | 863 | 136.7 | 9 | 0.158 |
| 11* | o/w | 200 g - 0.3% gelatin | 44 g oil | no gel | no gel | — | — |
| 12* | o/w | 200 g - 0.6% gelatin | 44 g oil | 1.24 | 0.26 | 4 | — |
| 13* | o/w | 200 g - 1.0% gelatin | 44 g oil | 25.3 | 1.77 | 4 | — |

*Comparison

EXAMPLE II

A series of w/o emulsions were prepared by emulsifying an aqueous solution (A) (50 g) into groundnut oil (50 g) using of Admul WOL (3 g) as emulsifier. Solution A contained sucrose (30% w/w) and various concentrations of KCl in the range 0.3% w/w to 3.0% w/w.

Emulsification was accomplished using a Silverson mixer under the conditions of example I. Three duplex emulsions were prepared at each potassium chloride level by emulsifying the water in oil emulsion (50 g, 70 g, 90 g) into 200 g of the external phase (B) at 25° C. using a Silverson mixer under the mild conditions of Example I.

The external phase (B) had the composition.

| | |
|---|---|
| Sucrose | 2 g |
| Sodium Caseinate | 2 g |
| K Carrageenan (L100) | 2 g |
| Distilled water | 194 g |
| | 200 g |

The duplex emulsion formed was stirred with a magnetic stirrer at slow speed until gelation occurred.

Similarly to example I the initial phase volumes of the w/o lay in the range 0.2–0.35. Simple osmotically driven swelling of the internal water phase would produce dispersed phase volumes in the appropriate range about 0.7–about 0.9. However, the release of some of the internal phase during preparation and osmotic swelling reduces the actual disperse phase volumes after swelling to less than this theoretical maximum. The results are given in Table III (amounts w/w).

TABLE III

| EXAMPLE | EXTERNAL PHASE | DISPERSE PHASE (W/O) | KCl CONC % W/W IN DISPERSED WATER PHASE | GELLING TIME |
|---|---|---|---|---|
| 14 | 200 g | 50 g | 3 | 7-8 mins |
| 15 | 200 g | 70 g | 3 | 5-6 mins |
| 16 | 200 g | 90 g | 3 | 2-3 mins |
| 17 | 200 g | 50 g | 1 | >120 mins |
| 18 | 200 g | 70 g | 1 | about 40 mins |
| 19 | 200 g | 90 g | 1 | about 20 mins |
| 20 | 200 g | 50 g | 0.3 | |
| 21 | 200 g | 70 g | 0.3 | several hrs |
| 22 | 200 g | 90 g | 0.3 | |

The gelled emulsion obtained under the conditions described above depends both on the swelling of the duplex droplets, to produce a high disperse phase volume, and on the release of potassium from some of the droplets. More independent control of the potassium release and the swelling is obtained when the sucrose and potassium are incorporated in separate droplets.

We claim:

1. A gelled duplex emulsion structure consisting essentially of:
   i) 0.1% to about 20% by weight of a gelled external continuous aqueous phase comprising a gelling component selected from gelatin, meat, egg protein, fish protein, gelling polysaccharides and clays;
   ii) oil or liquid fat component selected from olive oil, palm oil, groundnut oil, sunflower oil and animals fats dispersed in the external phase; and
   iii) an aqueous phase containing an osmotic pressure component selected from water-soluble salts, sugars, amino acids, peptides and ureas and dispersed in the oil or fat phase (ii).

2. A gelled duplex emulsion structure according to claim 1 wherein the gelled external continuous aqueous phase forms at least 1% by weight of the structure.

3. A composition comprising an active component and a release system or carrier, said release system or carrier being a gelled duplex emulsion according to claim 1.

4. A gelled duplex emulsion structure according to claim 1 containing from about 5% to about 30% by weight of the oil/fat component.

5. A gelled duplex emulsion structure according to claim 4 wherein the oil/fat component forms from about 10% by weight to about 20% by weight.

6. A gelled duplex emulsion structure according to claim 1 wherein the theoretical disperse phase volume is in the range about 0.7 to about 0.9.

7. A method of preparing a gelled duplex emulsion structure according to claim 1, wherein an emulsion of water in an oil or liquid fat selected from olive oil, palm oil, groundnut oil, sunflower oil and animals fats, having in the aqueous phase an osmotic pressure component selected from water-soluble salts, sugars, amino acids, peptides and ureas is dispersed in an aqueous solution of a gelling component selected from gelatin, meat, egg protein, fish protein, gelling polysaccharides and clays, causing the external continuous phase to gel by thermal or chemical means and the emulsion is retained until the external continuous phase has gelled.

8. A method of preparing a gelled duplex emulsion structure as claimed in claim 7 wherein the initial external phase contains from about 0.1% to about 5% by weight of gelling component.

9. A gelled duplex emulsion structure consisting essentially of:

i) 0.1% to about 40% by weight of a gelled external continuous aqueous phase comprising a gelling component selected from gelatin, meat, egg protein, fish protein, gelling polysaccharides and clays;
ii) oil or liquid fat component selected from olive oil, palm oil, groundnut oil, sunflower oil and animals fats dispersed in the external phase;
iii) an aqueous phase containing an osmotic pressure component selected from water-soluble salts, sugars, amino acids, peptides and ureas and dispersed in the oil or fat phase (ii);
iv) an internal emulsifier in a sufficient amount to stabilize the water in oil emulsion having a hydrophilic-lipophilic balance (HLB) of not more than 6; and
v) a sufficient amount of an external oil/water emulsifier having an HLB of at least 8.

* * * * *